United States Patent [19]

Robins et al.

[11] Patent Number: 5,583,261
[45] Date of Patent: Dec. 10, 1996

[54] ALICYCLIC DIAMINE FUNGICIDES

[75] Inventors: David J. Robins, Milton of Campsie; Dale R. Walters, Prestwick, both of Scotland

[73] Assignee: British Technology Group Ltd., London, England

[21] Appl. No.: 450,337

[22] Filed: May 25, 1995

Related U.S. Application Data

[62] Division of Ser. No. 325,210, Oct. 21, 1994, Pat. No. 5,464,873.

[30] Foreign Application Priority Data

May 28, 1992 [GB] United Kingdom ............... 9211291

[51] Int. Cl.$^6$ ................ C07C 211/15; C07C 211/18
[52] U.S. Cl. ........................................... 564/455
[58] Field of Search .................................. 564/455

[56] References Cited

U.S. PATENT DOCUMENTS

| | | | |
|---|---|---|---|
| 3,852,347 | 12/1974 | Krapcho | 564/53 |
| 4,132,792 | 2/1979 | Zinnes et al. | 424/250 |
| 4,370,484 | 1/1983 | Faulkner | 548/316 |

FOREIGN PATENT DOCUMENTS

| | | |
|---|---|---|
| 10896 | 5/1980 | European Pat. Off. |
| 2228395 | 9/1990 | Japan . |
| 826979 | 1/1960 | United Kingdom . |
| 1121413 | 7/1968 | United Kingdom . |
| 1164354 | 9/1969 | United Kingdom . |
| 2066819 | 7/1981 | United Kingdom . |

OTHER PUBLICATIONS

E. D. Middlemas and L. D. Quin, "A New Synthesis of the Isophosphindoline System", J. Org. Chem. 44, 2587–2589 (1989).

H. Suess and M. Hesse, "108 Stereospezifische Fragmentierung in den Massenspektren von Cyctohexandiaminen . . . ", Helv. Chim. Acta, 62, 1065–1077 (1979).

L. D. Quin et al., "3,3–Thionanedione 1,1–Dioxide . . . ", J. Org. Chem. 44, 3496–3500 (1979).

L. D. Quin et al., "Synthesis and Conformational Properties of 3,8–Phosphor 1–oxides", J. Amer. Chem. Soc. 104, 1893–1900 (1992).

T. A. Smith et al., "Growth Inhibition of Botrytis Cinerea by Compounds interfering with Polyamine Metabolism", J. Gen. Microbiology 136, 985–992 (1990).

A. Hosomi et al., "New Synthesis and Diels–Alder Reactions . . . ", Bull. Chem. Soc. Japan 64, 1051–1053 (1991).

D. Butina et al., "Synthesis of 1–Cyclopentene–1,2–dicarboxaldehyde . . . ", Jul. 1980, pp. 543–545.

Kirkemo et al., J. Org. Chem., vol. 50, pp. 1316–1319.

Peelen et al., Recl. Trav. Chim. Pays–Bas, vol. 105, pp. 326–331.

*Primary Examiner*—Richard L. Raymond
*Attorney, Agent, or Firm*—Nixon & Vanderhye

[57] ABSTRACT

Use of a compound having the general formula:

$$W \begin{array}{c} CH_x \\ || \\ CH_x \end{array} \begin{array}{c} CH_2-NR^1R^2 \\ \\ CH_2-NR^3R^4 \end{array} \quad (1)$$

wherein $R^1$, $R^2$, $R^3$ and $R^4$ which may be the same or different represent hydrogen atoms or alkyl groups of 1–6 carbon atoms, or $NR^1R^2$ and/or $NR^3R^4$ together represent a heterocyclic group having 5 or 6 ring atoms, x is 0 or 1 and when x is 0, the dashed line represents a double bond, W represents a saturated or ethylenically unsaturated divalent hydrocarbyl group required to complete a cycloalkane, cycloalkene or cycloalkadiene ring of 3 to 6 ring atoms and from 0 to 2 double bonds, in the form of the free base or an acid addition salt tolerable to plants, as a plant fungicide, as a fungicide, especially as a mildewicide.

Some of the compounds of formula (1) are new and are claimed per se.

3 Claims, No Drawings

ALICYCLIC DIAMINE FUNGICIDES

This is a Rule 60 Divisional of application Ser. No. 08/325,210, filed as PCT/93/01125, May 28, 1993, now U.S. Pat. No. 5,464,873.

FIELD OF THE INVENTION

This invention is in the field of the control of fungal infection in plants.

DESCRIPTION OF THE PRIOR ART

The effect of compounds which interfere with polyamine metabolism on the growth of the fungus *Botrytls cinerea* has been investigated, Smith et al., J. Gen. Microbiol. 136, 985 (1990). This work demonstrated that difluoromethylornithine, (DFMO) inhibition of fungal growth could be reversed with the addition of putrescine, cadaverine, spermidine and spermine. "Butenediamine" itself caused some inhibition of fungal growth but significantly reversed the inhibitory effect of DFMO.

SUMMARY OF THE INVENTION

We have now discovered that certain alicyclic diamines exhibit useful antifungal activity.

Accordingly, the invention provides the use of a compound having the general formula (1):

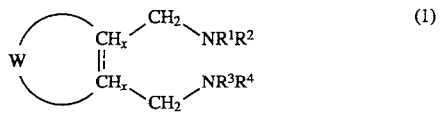

wherein $R^1$, $R^2$, $R^3$ and $R^4$ which may be the same or different represent hydrogen atoms or alkyl groups of 1–6 carbon atoms or $NR^1R^2$ and/or $NR^3R^4$ together represent a heterocyclic group having 5 or 6 ring atoms, the dashed line represents a double bond, W represents a saturated or ethylenically unsaturated divalent hydrocarbyl group required to complete a cycloalkane, cycloalkene or cycloalkadiene ring of 3 to 6 ring atoms, preferably 4 to 6 ring atoms, and from 0 to 2 double bonds, in the form of a free base or acid addition salt tolerable to plants, as a plant fungicide.

DESCRIPTION OF THE PREFERRED EMBODIMENTS

One class of preferred compounds of formula (1) is those wherein W completes a cycloalkane or cycloalkene ring of 4 to 6 ring atoms. W represents preferably a group having the formula —$(CH_2)_n$— wherein n is from 2 to 4 or a group —$CH_2$—$CHyR^5$---$CHyR^6$—$CH_2$— wherein y is 0 or 1 and when y is 0 the dashed line represents a double bond and $R^5$ and $R^6$ which may be the same or different represent hydrogen atoms or alkyl groups of 1 to 4 carbon atoms, especially methyl groups.

$R^1$, $R^2$, $R^3$ and $R^4$ are preferably alkyl groups of 1 to 4 carbon atoms, especially methyl, or hydrogen atoms.

One particularly preferred class of compounds for use as a plant fungicide is trans —N,N,N',N'-tetramethyl or —tetraethyl-1,2-bis(aminomethyl)cyclobutane [better named trans-1,2-bis(methylaminomethyl of ethylaminomethyl)cyclobutane] and also 1,2-bis(methylaminomethyl or ethylaminomethyl)cyclohexa-1,4-diene.

Others are the primary amines, ($R^1$, $R^2$, $R^3$ and $R^4$ are all hydrogen). Within this group, particularly preferred compounds are 1,2-bis(aminomethyl)-4,5-dimethylcyclohexa-1,4-diene and 1,2-dimethyl-4,5-bis(aminomethyl)cyclohex-1-ene, of which the trans isomer is more preferred than the cis isomer.

Preferred heterocyclic groups $NR^1R^2$ and/or $NR^3R^4$ are pyrrolidino, piperidino, 4-methylptperidino and morpholino.

All these diamines can form salts with mineral acids or organic acids. Preferred mineral acids are HCl, HBr, $HNO_3$, $H_2SO_4$, $H_3PO_4$. Preferred organic acids are propionic, benzoic, formic, acetic, trifluoroacetic, maleic, fumaric, succinic, malonic, tartaric, ascorbic, citric, oxalic, glyoxalic, alkyl or anyl sulphonic. These salts may be prepared by standard techniques and procedures well known in the art.

The compounds of the invention may be prepared by conventional techniques in organic chemistry and/or techniques analogous to those of the Examples herein, e.g. substituting pyrrolidine or morpholine for aliphatic amines.

The diamine compounds of the invention also exhibit antifungal activity when prepared in the form of their acid salts and such salts may be used as fungicides according to this invention. The compounds of the invention are particularly useful fungicides against fungi of the genera Erysiphe and Podosphaera. These fungi cause mildew in plants. Thus the compounds of the invention are particularly useful mildewicides.

This invention also provides fungicidal compositions comprising the diamine compound together with a suitable diluent or carrier. Such diluents or carriers must not be phytotoxtc to the plant materials. Suitable diluents or carriers include water and organic solvents. Preferably the concentration of diamine is between 0.001 to 0.1 molar.

Thus, the diamine can be dispersed on a finely-divided solid carrier to form a dusting powder. Also, the amine can be dispersed in water, typically with the aid of a wetting agent, and the resulting aqueous dispersion employed as a spray. In other procedures the amine can be employed as a constituent of organic liquid compositions, oil-in-water and water-in-oil emulsions or dispersions, with or without the addition of wetting, dispersing or emulsifying agents.

Suitable adjuvants of the foregoing type are well known to those skilled in the art.

The choice of such diluents, carriers and wetting agents (if required) will vary, depending upon the type of composition required for specific purposes and may be different for compositions intended to treat fields of crops or those compositions used for treating individual plants. The choice of such diluents or carriers and wetting agents will however be apparant to those skilled in the art. The methods of applying the solid or liquid fungicidal formulations are similarly well known.

The present invention also provides a method for the fungicidal treatment of plant material in either a preventative or curative mode using antifungal diamine compounds as described hereinbefore. The treatment may be applied to growing or harvested plant materials. If the plant material is growing, then the plants may be treated before they are infected by the fungi. This can be carried out by either treating the whole plant (e.g. by spraying it with a solution/emulsion or suspension on the antifungal compounds) or on specific parts of the plant, e.g. the leaves, stems, fruits or even seeds prior to planting. Treatment of the soil is another alternative since the antifungal compounds of the invention are systemic in their mode of action. Plants which have come into contact with fungi and thus already infected may be treated locally at site of infection or the whole plant may be treated.

The present invention also includes treatment of harvested plant parts for the prevention or control of fungal diseases. For this, various ways of carrying out the treatment can be employed. These will be well known to those skilled in the art, for example, treatment can be to the harvested plant itself by for example dipping the plant part into a solution of the antifungal agent, or by impregnating fungicide into the wrapper, carton, crate, etc., in which the plant will be transported. Alternatively, the harvested plant material may be fumigated with the fungicide in a special room, car or tank.

A typical solid composition may be formulated by dry milling the active compound with BARDEN clay. This solid formulation or dust can contain the active compounds in amounts of from about 1 to about 25 percent by weight or more if desired. The dust is suitable for application to cereal seeds prior to planting.

A typical liquid composition is formulated by dissolving the active compound in a mixture of water and isopropanol (80:20 water/isopropanol ratios) containing a surfactant. This liquid formulation can contain the active compound in amounts of from about 15 to about 40 percent by weight or more if desired. The aqueous formulation is suitable for application to cereal foliage or application as a seed drench, after suitable dilution with water.

The concentration of the active compounds in solid or liquid compositions is dependent upon the use, but for agricultural purposes generally is from about 1 to about 20 percent by weight or more. Concentrations from about 5 to about 10 percent by weight are often employed. In compositions to be employed as concentrates, the active compound can be present in a concentration from about 15 to about 50 weight percent, preferably 20 weight percent. The compositions containing the active compounds can also contain other compatible additives, for example when used in an agricultural context, phytotoxicants, plant growth regulants, pesticides, film-forming anti-transpirants, other fungicides and the like which are suitable for application to agricultural, horticultural, forestry and amenity crops. The present compositions can be applied to plants and crops by the use of power dusters, boom and hand sprayers, spray dusters and by other conventional means. The compositions can also be applied from airplanes as a dust spray since the ingredients are effective at very low application rates.

The exact rate to be applied is dependent not only on the specific amine being applied, but also on the particular treatment desired (e.g. animals, seeds, soil, or foliage) the particular crop being treated, climatic conditions, severity of any infection and the like. Thus, it is also to be understood that all of the active compounds of the present invention and compositions containing the same may not be equally effective at similar concentrations or against the same fungal species.

In foliar treatments, the active compounds of the present invention are usually applied at an approximate rate of from about 50 to 500 g/ha, a rate of from about 100 to 400 g/ha being preferred and a rate of from about 100 to about 350 g/ha being particularly preferred.

In seed treatments, the active compounds of the present invention are usually applied at an approximate rate of from about 60 to about 250 g per 100 kg seed, a rate of from about 100 g to about 200 g per 100 kg seed being preferred and a rate of from about 140 to about 180 g per 100 kg seed being particularly preferred. Seeds may be treated prior to planting and this may be carried out among other methods by fumigation.

In soil treatments, the active compounds of the present invention are usually applied at an approximate rate of from about 50 to about 350 g/ha, a rate of from about 100 to about 300 g/ha being preferred and a rate of from about 200 to about 280 g/ha being particularly preferred.

There are also provided fungicidal compositions comprising at least one diamine compound of formula (1) together with a suitable carrier, diluent and preferably a wetting agent. Such carriers, diluents and wetting agents must not be phytotoxic to plant materials when used in an agricultural context when the diamine is present at a fungicidal concentration. Suitable diluents and carriers include water and organic solvents, wherein the total concentration of the diamine compound or compounds is between 0.001 to 0.1 molar.

Many compounds of formula (1) above are novel per se. Thus, the current invention extends to all such compounds, in particular those of the general formula (1) above, wherein $R^1$, $R^2$, $R^3$ and $R^4$ which may be the same or different represent hydrogen atoms or alkyl groups of 1–6, preferably 1–4, carbon atoms, or $NR^1R^2$ and/or $NR^3R^4$ together represent a heterocyclic group having 5 or 6 ring atoms and W represents a group of formula —$(CH_2)_n$— wherein n is 2 or 3 (thus completing a cyclobutane, cyclobut-1-ene, cyclopentane or cyclopent-1-ene ring) or of formula —$CH_2$—$CHyR^5$—$CHyR^6$—$CH_2$— wherein y is 0 or 1 and when y is 0 the dashed line represents a double bond, the sum of x and y is 1 or 2 (whereby W thus completes a cyclohexene or cyclohexadiene ring) and $R^5$ and $R^6$, which may be the same or different, represent hydrogen atoms or alkyl groups of 1 to 4 carbon atoms, in the form of the free base or as an acid addition salt tolerable to plants.

A particularly preferred compound of the above formula is trans-1,2-dimethyl-4,5-bis(aminomethyl)cyclohex-1-ene and its said salts.

EXAMPLES

This invention is illustrated by way of the following Examples. "Tween", "Celite", "Mistral" and "Bayfidan" are Registered Trade Marks.

EXAMPLE 1

Synthesis of 1,2-bis(aminomethyl)cyclopent-1-ene dihydrochloride.

A. 1,2-Bis(hydroxymethyl)cyclopent-1-ene

The title compound is known from D. Butina and F. Sondheimer, Synthesis 543–545 (1980). It was synthesised in 22% overall yield in three steps from pimelic acid (heptane-1,7-dioic acid) following the procedure of that paper. N.m.r: δH (90 MHz, $CDCl_3$) 4.21 (s,4H), 3.51 (bs,2H), 2.47 (t,4H), 1.83 ppm (m,2H).

B. 1,2-Bis(aminomethyl)cyclopent-1-ene dihydrochloride

To a solution of hydrazoic acid (1.25M) in benzene (19 ml) was added 1,2-bis(hydroxymethyl)cyclopent-1-ene (1.28 g, 0.01 mol) in dry THF (20 ml), and diisopropyl azodicarboxylate (2.52 g, 0.025 mol) in dry THF (10 ml). To this stirred solution was added triphenylphosphine (10.48 g, 0.05 mol) in dry THF (35 ml) over 1 hour. The mixture was then stirred at 50° C. for a further 16 hours, then water (5 ml) added. The mixture was allowed to cool, then partitioned between hydrochloric acid (1M, 100 ml) and $CH_2Cl_2$. (100 ml) The aqueous layer was further washed with $CH_2Cl_2$ (2×80 ml), and the water removed in vacuo to give a brown solid, which was recrystallised twice (ethanol/acetone) to give the title compound, yield 21%. N.m.r: δH (90 MHz, D$_2$O) 4.05 (s,4H), 2.39 (t.4H), 1.89 ppm (m,2H)

EXAMPLE 2

Synthesis of 1,2-bis(aminomethyl)-4,5-dimethylcyclohexa-1,4-diene hydrochloride

A. Dimethyl 4,5-dimethylcyclohexa-1,4-diene-1,2-dicarboxylate 2,3-dimethylbutadiene (9.84 g, 0.12 mol) and dimethyl acetylenedicarboxylate (14.2 g, 0.1 mol) were stirred together in water (50 ml) at 60° C. for 24 hours. The emulsion was cooled to room temperature and filtered. The filtered solid was recrystallised from diethyl ether to give the title compound in 78% yield. N.m.r: δH (90 MHz, CDCl$_3$) 3.70 (s,6H), 1.71 ppm (s,6H)

B. 1,2-Bis(hydroxymethyl)-4,5-dimethylcyclohexa-1,4-diene

To a solution of DIBAL in dichloromethane (1.0M, 45 ml, 0.045 mol) cooled to ice bath temperature under nitrogen was added dimethyl 4,5-dimethylcyclohexa-1,4-diene-1,2-dicarboxylate (2.24 g, 0.01 mol) in dry dichloromethane (30 ml) over 30 min. The resultant solution was stirred for a further 60 mins at this temperature after which methanol (10 ml) was added. The mixture was allowed to come to room temperature, filtered through a "Celite" pad, and the filtrate concentrated in vacuo to give an oil. Crystallisation from ethyl acetate/petroleum ether (40°–60° C.) gave the title compound in 35% yield. N.m.r: δH (90 MHz, CD$_3$OD) 4.15 (s,4H), 3.55 (bs,2H), 2.82 (s,4H), 1.69 ppm (s,6H)

C. Synthesis of 1,2-Bis(aminomethyl)-4,5-dimethylcyclohexa-1,4-diene hydrochloride The procedure of Example 1 was repeated using 1,2-bis(hydroxymethyl)-4,5-dimethyl-1,4-cyclohexadiene as the starting diol. The title compound was obtained in 32% yield. N.m.r: δH (90 MHz, D$_2$O) 3.98 (s,4H), 2.85 (s,4H), 1,62 ppm (s,6H)

EXAMPLE 3

Synthesis of 1,2-bis(aminomethyl)cyclohex-1-ene dihydrochloride

A. Dimethylcyclohex-1-ene-1,2-dicarboxylate 3,4,5,6-tetrahydrophthalic anhydride (3.04 g, 0.02 mol) was disolved in methanol (25 ml) and refluxed for 2 hours. The solution was then cooled to ice bath temperature and a solution of diazomethane in diethyl ether was added dropwise until a yellow colour persisted. The solution was then allowed to stand overnight, after which time the solvent was removed in vacuo to give the title compound in 93% yield. δH (90 MHz, CDCl3) 3.66 (s,6H), 2.20 (s,4H), 1.66 ppm (s,6H)

B. 1,2-Bis(aminomethyl)cyclohex-1-ene dihydrochloride

The procedure for conversion of the above ester into the title compound was as described in Example 2 above. The title compound was produced in 12% overall yield. N.m.r: δH (90 MHz, D$_2$O) 4.00 (s,4H), 2.15 (m,4H), 1.60 ppm (m,4H).

EXAMPLE 4

Synthesis of trans-1,2-dimethyl-4,5-bis(aminomethyl)cyclohex-1-ene

A. Trans-4,5-bis(hydroxymethyl)-1,2-dimethylcyclohex-1-ene

To a suspension of lithium alumium hydride (1.529 g, 0.04 mol) in dry THF (60 ml) at 0° C. was added trans-dimethyl 1,2-dimethylcyclohex-1-ene-4,5-dicarboxylate (2.269 g, 0.01 mol) in dry THF (40 ml) over 30 min. The resultant suspension was stirred for another hour at 0° C., and then saturated sodium sulphate solution (5ml) was added dropwise. The solution was filtered and the filtrate evaporated to give an oil, which on purification gave the title compound in 36% yield. N.m.r: δH (90 MHz, CDCl$_3$) 3.70 (m,4H), 3.55 (bs,2H), 2.02 (m,4H), 1.96 (m,2H), 1.64 ppm (s,6H).

B. Trans-4,5-bis(aminomethyl)-1,2-dimethylcyclohex-1-ene dihydrochloride

The procedure of Example 1 above was repeated using trans-4,5-bis(hydroxymethyl)-1,2-dimethylcyclohex-1-ene as the starting diol. The title compound was obtained in 22% yield. N.m.r: δH (90 MHz, D$_2$O) 3.42 (m,4H), 2.05 (m,4H), 1.80 (m,2H), 1.66 ppm (s,6H).

EXAMPLE 5

Synthesis of cis-4,5-bis(aminomethyl)-1,2-dimethylcyclohex-1-ene dihydrochloride A. Cis-1,2-dimethylcyclohexene-4,5-dicarboxylic anhydride Maleic anhydride (9.8 g, 0.10 mol) and 2,3-dimethylbutadiene (9.84 g, 0.12 mol) were mixed in toluene (50 ml) for 24 h at 50° C. The solution was allowed to cool, the solvent removed in vacuo and the residue recrystallised from petroleum ether (40° C.–60° C.) to yield the title compound in 92% yield. N.m.r: δH (90 MHz, CDCl$_3$) 2.60 (m,2H), 2.14 (m,4H), 1.74 (s,6H).

B. Cis-4,5-bis(aminomethyl)-1,2-dimethylcyclohex-1-ene dihydrochloride

The procedures for the conversion from the anhydride into the title compound were as described in Example 3. Overall yield 6%. N.m.r: δH (90 MHz, D$_2$O) 3.37 (m,4H), 2.02 (m,4H) 1.76 (m,2H), 1.65 (s,6H).

EXAMPLE 6

Synthesis of trans-4,5-bis(diethylaminomethyl)-1,2-dimethylcyclohex-1-enedihydrochlride A. Trans-dimethyl 1,2-dimethylcyclohex-1-ene-4,5-dicarboxylate 2,3-dimethylbutadiene (9.84 g, 0.12 mol) and dimethyl fumarate (14.4 g, 0.1 mol) were stirred together in toluene (40 ml) at 50° C. for 24 hr. The solvent was removed in vacuo and the solid residue recrystallised from diethyl ether, to give the title compound in 85%, yield. N.m.r: δH (90 MHz, CD$_3$OD) 3.71 (s,6H), 2.55 (m,2H), 2.10 (m,4H), 1.74 ppm (s,6H).

B. Trans-1,2-dimethylcycohex-1-ene-4,5-dicarboxylic acid

Trans-dimethyl 1,2-dimethylcyclohex-1-ene-4,5-dicarboxylate (4.52 g, 0.02 mol) was refluxed with NaOH (4.0 g, 0.1 mol) in methanol (40 ml) for 4 hr. The solution was allowed to cool and partitioned between aqueous NaOH (2M, 50 ml) and ether (60 ml). The aqueous layer was then acidified (1M HCl) and extracted with ethyl acetate (3×50 ml). The solvent was removed in vacuo to give the title compound in 77% yield. N.m.r: δH (90 MHz CD$_3$Cl$_3$) 2.58 (m,2H), 2.08 (m,4H), 1.70 ppm (s,6H)

C. Trans-N,N,N',N'-tetraethyl-1,2-dimethylcyclohex-1-ene-4,5-dicarboxamide

To trans-1,2-dimethylcyclohexene-4,5-dicarboxylic acid (1.98 g, 0.0 mol) heated to 80° C., was added thionyl chloride (2.38 g, 0.02 mol) over 1 hr. The mixture was kept at this temperature for a further two hours, then cooled and added dropwise to a diethyl ether solution (45 ml) of excess diethylamine (14.6 g, 0.2 mol) cooled to ice bath temperature.

The solvent was removed to give the crude product as an oil which was not purified for use in the next stage.

D. Trans-N,N,N',N'-tetraethyl-4,5-bis(aminomethyl)-1,2-dimethylcyclohex-1-ene dihydrochloride -trans=4,5-bis(diethylaminomethyl)-1,2-dimethylcyclohex-1-ene dihydrochloride The crude diamide (1.54 g, 0.005 mol) in THF (25 ml) was added to a suspension of lithium aluminium hydride (0.76 g, 0.02 mol) in THF (30 ml) at 25° C. over 30 min. The resultant suspension was stirred for a further two hours at this temperature, then saturated sodium sulphate solution (5 ml) was added. The solution was filtered, and partitioned between diethyl ether (50 ml) and hydrochloric acid (1M, 50 ml). The aqueous layer was further extracted with dichloromethane (2×50 ml), and the water removed in vacuo to leave a brown solid, which was recrystallised to give the title compound in 5% overall yield. N.m.r: $\delta$H (90 MHz, $D_2O$) 3.30 (m,12H), 2.14 (m,4H), 1.70 ppm (m,20H)

EXAMPLE 7

Synthesis of trans-N,N,N',N'-tetramethyl-1,2-cyclohexanebis(methanamino)dihydrochloride=trans-1,2-bis(dimethylaminomethyl)cyclohexane hydrochloride This synthesis was carried out by adapting the procedure described in L. D. Quin et al., J. Org. Chem. 44, 3496–3500 (1989) used to prepare cis-1,2-bis(dimethylamtnomethyl)cyclohexane.

A. Trans-N,N,N',N'-tetramethyl-1,2-cyclohexanedicarboxamide

Synthesis was followed as Quin et al. to give a white-solid (20% yield). N.m.r: $\delta$H (200 MHz, $CDCl_3$) 1.37 (4H,m) 1.82 (4H,m), 2.65(2H,m), 2.89 (6H,s) and 3.10(6H,s).

B. Trans-N,N,N',N'-tetramethyl-1,2-cyclohexanebis(methanamine)

Again the procedure was followed as in Quin et al. to give a yellow oil (17% yield). N.m.r: $\delta$H (90 MHz, $CDCl_3$) 1.3 (4H,m) 1.8–2.3(6H,m), 3.0–3.2 (16H,m).

C. Trans-N,N,N',N'-tetramethyl-1,2-cyclohexanebis(methanamino) dihydrochloride=trans-1,2-bis(dimethylamtnomethyl)cyclohexane dihydrochloride The free base was stirred with ethereal HCl for 2 hours. to produce the required hydrochloride salt (90% yield). N.m.r: $\delta$H (90 MHz, $D_2O$) 1.3 (4H,m), 1.8 (6H,m), 2.9–3.3 (16H,m).

EXAMPLE 8

Synthesis of trans-1,2-bis(dimethylamlnomethyl)cyclobutane dihydrochloride

The procedure described above in Example 7 was repeated using trans-1,2-butanedicarboxylic acid, and a yellow solid was isolated as the hydrochloride salt in 10% overall yield. N.m.r: $\delta$H (90 MHz, $CD_3OD$) 1.6–2.5 (6H,m), 2.7(16H,m).

EXAMPLE 9

Effect of 1,2-bis(aminomethyl)-4,5-dimethylcyclohexa-1,4-diene ("BAD") on powdery mildew infection of barley seedlings The effect of the alicyclic polyamine analogue, BAD on powdery mildew infection of barley was studied. Seeds of barley (*Hordeum vulgare* L. cv Golden Promise) were sown in Fisons Levington compost in 36 cm seed trays. Plants were grown in a glasshouse under natural daylight supplemented for 16 hours dally by 400 W mercury vapour lamps. The maximum temperature was 24° C. during the day and fell to a minimum of 9° C. at night. Plants at growth stage 12 (second leaf unfolded, Zadok's scale) were used in experiments. Seedlings were sprayed to run-off with solutions of the compounds containing 0.01% Tween 20. In all cases solutions were adjusted to pH 7.0 prior to spraying (using either sodium hydroxide or HCl). Sprays were applied using a Shandon spray unit either before or after inoculation with powdery mildew. Plants were inoculated with mildew conidia by shaking infected stock plants over them. Intensity of infection was assessed 6, 8 and 10 days after inoculation by estimating the percentage leaf area infected using a standard area diagram. Barley powdery mildew normally sporulates 6–7 days after inoculation.

BAD, applied to barley seedlings as a 1 or 5 mM spray, pre- or post-inoculation, gave excellent control of powdery mildew. 1 mM BAD applied post-inoculation reduced mildew infection by 94%. This experiment was repeated three times with the same result.

The results of this experiment are shown in Tables 1 and 2 below.

TABLE 1

Effects of BAD on infection of barley seedlings with powdery mildew pre-inoculation.

| Treatment | % powdery mildew infection days after inoculation | | |
|---|---|---|---|
| | 6 | 8 | 10 |
| Control | 5.3 ± 1.1 | 10.1 ± 1.8 | 13.8 ± 1.7 |
| BAD, 1 mM | 2.1 ± 0.2 | 2.8 ± 0.5 | 5.4 ± 0.7 |
| BAD, 5 mM | 0.6 ± 0.1 | 1.6 ± 0.3 | 2.9 ± 0.4 |

TABLE 2

Effects of BAD on infection of barley seedlings with powdery mildew post-inoculation.

| Treatment | % powdery mildew infection days after inoculation | | |
|---|---|---|---|
| | 6 | 8 | 10 |
| Control | 24.5 ± 1.6 | 43.2 ± 2.6 | 55.0 ± 3.1 |
| BAD. 1 mM | 2.5 ± 0.3 | 3.5 ± 0.4 | 3.9 ± 0.4 |
| BAD, 5 mM | 0.6 ± 0.1 | 2.0 ± 0.2 | 2.8 ± 0.4 |

EXAMPLE 10

Tests for systemic action of BAD-Root Drench Tests

Barley seedlings were grown and the experiments were carried out as described in Example 9.

BAD applied as a pre-inoculation or a post-inoculation root drench resulted in some reduction in mildew infection. Mildew control was less pronounced for the pre-inoculation treatment, but was more substantial for post-inoculation treatments (72% reduction in mildew if applied 1 d after inoculation). Thus, BAD has xylem mobility and does give mildew control especially if applied as a post inoculation drench.

The results are shown in Table 3 below:

TABLE 3

Effects of BAD, applied as a root drench, on mildew infection of barley seedlings. All treatments applied at 1 mM.

| Treatment | % mildew infection days after inoculation | | |
|---|---|---|---|
| | 6 | 8 | 10 |
| Pre- and post-inoculation root drench | | | |
| Control | 12.6 ± 1.2 | 25.0 ± 2.4 | 32.5 ± 1.8 |
| BAD, 1 d pre | 12.7 ± 1.3 | 20.5 ± 2.8 | 36.5 ± 2.3 |
| BAD, 2 d pre | 11.2 ± 1.8 | 17.4 ± 2.0 | 28.5 ± 4.1 |
| BAD, 5 d pre | 12.6 ± 1.2 | 23.8 ± 1.5 | 30.0 ± 3.1 |
| Control | 3.5 ± 0.4 | 6.4 ± 0.6 | 8.3 ± 0.8 |
| BAD, 1 d post | 2.0 ± 0.2 | 3.1 ± 0.4 | 4.9 ± 0.5 |

TABLE 3-continued

Effects of BAD, applied as a root drench, on mildew infection of barley seedlings. All treatments applied at 1 mM.

| Treatment | % mildew infection days after inoculation | | |
|---|---|---|---|
| | 6 | 8 | 10 |
| BAD, 2 d post | 2.0 ± 0.2 | 1.9 ± 0.2 | 2.5 ± 0.3 |
| BAD, 5 d post | 2.2 ± 0.3 | 3.0 ± 0.4 | 5.5 ± 0.7 |

EXAMPLE 11

Effects of applying BAD to the lower leaves on powdery mildew infection on the upper leaves of barley seedlings Barley seedlings were grown and the procedure carried out was as described in Example 9 hereinbefore.

The results are shown in Table 4 below.

Application of 1 mM BAD to the lower leaves 1, 2 or 5 days after inoculation of the upper leaves provided no control of powdery mildew.

TABLE 4

Effects of BAD, applied to lower leaves, on powdery mildew infection on the upper leaves of barley seedlings. BAD was applied as a post inoculation treatment at 1 mM, 1, 2 or 5 days after inoculation of the upper leaves with mildew.

| Treatment | % mildew infection days after inoculation | | |
|---|---|---|---|
| | 6 | 8 | 10 |
| Control | 8 ± 1 | 11 ± 1 | 18 ± 2 |
| BAD, 1 d post | 7 ± 1 | 11 ± 1 | 20 ± 3 |
| BAD, 2 d post | 8 ± 1 | 15 ± 1 | 23 ± 2 |
| BAD, 5 d post | 7 ± 1 | 14 ± 1 | 19 ± 2 |

EXAMPLE 12

Effects of timing of the application of BAD on control of barley powdery mildew

Barley seedlings were grown and the procedure for the experiments was carried out as described in Example 9. However in this example, the experiments were conducted in order to investigate the effects of timing of the application of BAD to the seedlings at different times, before or after inoculation with the pathogen. The results are shown in Table 5 below.

TABLE 5

Effects of application at different times before or after inoculation, on powdery mildew infection of barley seedlings. All compounds applied at 1 mM. Assessments were made 6, 8 and 10 days after inoculation, but only the assessment on day 10 is shown.

| | % mildew infection |
|---|---|
| Control | 31.0% 2.55 |
| 5 d pre-inoculation BAD | 20.0% 0.8 |
| 2 d pre-inoculation BAD | 20.0% 4.3 |
| 1 d pre-inoculation BAD | 22.8% 2.4 |
| 1 d post-inoculation BAD | 11.0% 1.0 |
| 2 d post-inoculation BAD | 6.8% 1.2 |
| 5 d post-inoculation BAD | 11.1% 1.9 |

Although BAD reduced mildew infection irrespective of the timing of application, it was markedly less effective if applied prior to inoculation with the fungus. On the other hand, application after mildew inoculation gave very good control of mildew. It appears, therefore, that BAD has very little protective action against barley mildew, but does possess considerable curative action.

EXAMPLE 13

Effects of BAD on infection of barley seedlings by fungicide resistant strains of powdery mildew.

The effectiveness of 1 mM BAD on infection of barley seedlings by fungicide resistant strains of powdery mildew was examined. Again, Example 9 outlines the procedures followed. Three strains of barley powdery mildew were used, all supplied by the John Innes Centre for Plant Science Research, Cambridge Lab, Norwich, England:

cc-146 resistant to ethirimol and triadimenol cc-138 resistant to triadimenol cc-139 resistant to fenpropidin and fenpropimorph BAD gave very good control of all of the strains of powdery mildew. In contrast, the fungicides "Mistral" (containing fenpropimorph) and "Bayfidan" (containing tridaimenol) gave poor control of strains cc-139 and cc-138 respectively.

EXAMPLE 14

Comparison of the effects of BAD with commercial fungicides, on powdery mildew infection of barley seedlings BAD (1 mM) was compared with the following active ingredients of commercial fungicides (all used at 0.1%): propiconazole, tridemorph, flutriafol, fenpropidin.

Method

Barley seedlings (*Hordeum vulgate* L. CV Golden Promise) were sown in Ftsons Levington compost in 36 cm in seed trays. Plants were grown in a glasshouse under natural daylight supplemented for 16 h daily by 400 W mercury vapour lamps. The maximum temperature was 24° C. during the day and fell to a minimum of 9° C. at night. Plants at growth stage 12 (second leaf unfolded, Zadok's scale) were used in the experiments. Seedlings were sprayed to run-off with solutions of BAD at a concentration of 1 mM containing 0.01% "Tween" 20. In all cases solutions were adjusted to pH 7.0 prior to spraying (using either sodium hydroxide or HCl).

Solutions were sprayed onto seedlings until run off using a Shandon spray unit. Plants were inoculated with powdery mildew conidia by shaking infected stock plants over them. Intensity of infection was assessed 7 and 10 days after inoculation by estimating the percentage leaf area infected using a standard diagram. Sporulation usually occurred about 6–7 days after inoculation.

The results are shown in Table 6 below. Application of 1 mM BAD as a post-inoculation spray to barley seedlings provided mildew control that was as good as that achieved with 0.1% propiconazole or tridemorph. Mildew control using BAD (78% control) was greater than that obtained using flutriafol (49%).

TABLE 6

Comparison of the effects of BAD with the active ingredients of commercial fungicides on powdery mildew infection of barley seedlings. Mildew was assessed 10 days after inoculation.

| Treatment | % powdery mildew infection |
|---|---|
| Control | 4.5 |
| BAD, 1 mM | 1.0 |
| Propiconazole, 0.1% | 0.9 |
| Tridemorph, 0.1% | 0.8 |
| Flutriafol, 0.1% | 2.3 |
| Penpropidin, 0.1% | 0.6 |

EXAMPLE 15

Effect of BAD on infection of apple seedlings with the powdery mildew fungus Podosphaera leucotricha.

The effects of different concentrations of BAD, applied either as pre-inoculation or post-inoculation treatments, against the apple powdery mildew pathogen, *Podosphaera leucotricha*, were examined. Seeds of apple (*Malus bitenfelder*) were stratified by placing in a cold store for 14 weeks in trays of Fison's Levington compost. After 14 weeks the seeds were removed from cold storage and after 10 days those which had germinated were potted into individual 4 cm pots. After a further 12 days, the seedlings were inoculated by gently brushing spores of the apple powdery mildew fungus *Podosphaera leucotricha* on to the leaves. Three days after Inoculation, the seedlings were sprayed to run off with a solution of BAD (1 or 5 mM) using a Shandon spray unit. Inhibitor solutions were prepared in 0.01% "Tween" 20 and the pH adjusted to 7.0 using sodium hydroxide. Intensity of infection was assessed 13, 15 and 17 days after inoculation by estimating the percentage leaf area infected.

The results are shown in Table 7 below. BAD at 1 and 5 mM, applied before or after inoculation, gave very good control of apple powdery mildew. This suggests that against apple mildew, BAD possesses powerful protective and curative action (cf. barley mildew in Example 12).

TABLE 7

Effects of different concentrations of BAD, applied before or after inoculation, on powdery mildew infection of apple seedlings. Only the final asessment, 17 days after inoculation, is shown.

| Treatment | Infection index |
| --- | --- |
| Control | III |
| BAD 1 mM pre-inoculation | I |
| BAD 5 mM pre-inoculation | I |
| BAD 1 mM post-inoculation | I |
| BAD 5 mM post-inoculation | I |

Assessment Key
 0=no infection
 I=infection just visible
 II=infection area <50%
 III=infection area >50%

EXAMPLE 16

Effect of BAD on infection of broad bean seedings with the chocolate spot fungus, Botrytis fabae.
Method Seeds of broad bean (*Vicia faba* cv Express Long Pod) were sown in Fison's Levington compost in 15 cm plastic pots. Plants were grown in a ventilated glasshouse under natural daylight supplemented to a 16 h photoperiod with 400 W mercury vapour lamps. The maximum daylight temperature was 24° C., falling to a minimum of 9° C. at night.

Twenty day-old plants were sprayed to run-off with solutions of BAD (1 or 5 mM) before or after inoculation with spores of *Botrytis fabae*. Solutions were prepared in 0.01% "Tween" 20, with the pH adjusted to 7.0 with sodium hydroxide. Control plants were sprayed with "Tween" 20 (0.01%) only. After inoculation with a spore suspension, plants were loosely covered in plastic bags for 48 h to maintain the high relative humidity necessary for spore germination.

Plants to be given a pre-inoculatory treatment were sprayed with the inhibitors and left to dry for 2 h before inoculation. For post-inoculatory treatments, plants were inoculated and left for 2 days before application of the inhibitor. Intensity of infection was assessed 3, 5 and 7 days after inoculation by estimating the percentage leaf area infected using a standard area diagram.

The results are shown in Table 8 below. Pre- and post-inoculation sprays of BAD (1 and 5 mM) gave moderate control of chocolate spot on broad beans. Thus, a pest inoculation spray of 1 mM BAD reduced chocolate spot injection by 42%.

TABLE 8

Effects of BAD on infection of broad bean by the chocolate spot fungus *Botrytis fabae*

| Treatment | % leaf area infected |
| --- | --- |
| Pre-inoculation sprays | |
| Control | 34.1 |
| 1 mM BAD | 23.7 |
| 5 mM BAD | 20.0 |
| Post-inoculation sprays | |
| Control | 22.4 |
| 1 mM BAD | 20.0 |
| 5 mM BAD | 28.7 |

EXAMPLE 17

Effect of BAD on infection of broad beans with the rust fungus, Uromyces viciae-fabae.
Method These experiments were performed using the method described above in Example 16 for infection of beans with *Botrytis fabae*. For the rust experiments, BAD was used at 1 and 5 mM concentrations and assessment of intensity of infection was carried out 12, 15 and 18 days after inoculation. The results are shown in Table 9 below.

TABLE 9

Effects of a post-inoculation treatment with BAD on infection of faba beans by the rust fungus, *Uromyces viciae-fabae*.

| | % rust infection days after inoculation | | |
| --- | --- | --- | --- |
| Treatment | 12 | 15 | 18 |
| Control | 19.1 ± 2.5 | 22.5 ± 3.2 | 26.6 ± 4.0 |
| BAD, 1 mM | 20.4 ± 2.5 | 24.4 ± 2.8 | 25.4 ± 3.3 |
| BAD, 5 mM | 21.6 ± 3.9 | 22.0 ± 3.8 | 24.0 ± 4.5 |

EXAMPLE 18

Effects of the alicyclic diamines of Examples 3–5 on powdery mildew infection of barley seedlings.

The method followed was as described in Example 9 hereinbefore. The results are shown in Table 10 below. Post-inoculation treatment with the Ex.4 compound at 1 mM provided substantial control of powdery mildew infection on barley seedlings.

TABLE 10

Effects of alicyclic diames of Exampls 3–5 on powdery mildew infection of barley seedlings. Mildew was assesed 10 days after inoculation.

| Treatment | % powdery mildew infection |
| --- | --- |
| Control | 13.9 + 0.8 |
| Cpd. of Ex. 4, 1 mM | 4.7 + 0.3 |
| Control | 16.0 + 2.0 |
| Cpd. of Ex. 5, 1 mM | 12.6 + 1.4 |
| Cpd. of Ex. 3, 1 mM | 16.5 + 1.1 |

EXAMPLE 19

Effects of the compound of Ex. 4 on infection of potato leaf discs with the blight fungus Phytophthora infestans.

Potato leaf discs were floated on a solution of BAD at 1 mM and 5 mM concentration in a petri dish. They were then inoculated with sporangia of the blight fungus *Phytophthora infestans* and the covered petri dishes were then incubated for 6 days. The results are shown in Table 11 below. The compound of Example 4 at 1 and 5 mM provided moderate control of blight infection of potato leaf discs.

TABLE 11

Effects of the compound of Example 4 on infection of potato leaf discs with *Phytophthora infestans*.

| Treatment | Infection index* |
| --- | --- |
| Control | 5 |
| Cpd. of Ex. 4, 1 mM | 3.5 |
| Cpd. of Ex. 4, 5 mM | 2.5 |

*Infection index:
5 leaf disc covered with blight
0 no blight on leaf disc

EXAMPLE 20

Effects of the compounds of Examples 1, 6, 7 and 8 on powdery mildew infection of barley seedlings.

The experimental procedure followed was as described in Example 9 hereinbefore. The results are shown in Table 12 below.

The compounds were applied as post-inoculation sprays and the results presented here are infection intensities at 6 days after inoculation. All compounds reduced mildew infection significantly. The smallest reduction in mildew was achieved using the compound of Example 6 (58%), at the low concentration specified, while the greatest reduction in mildew infection was obtained using the compound of Example B (75%), at a higher concentration.

TABLE 12

| Treatment | | % mildew infection |
| --- | --- | --- |
| Control | | 3.36 ± 0.24 |
| Compound of Ex. 7 | (1.23 mM) | 0.93 ± 0.11 |
| Compound of Ex. 8 | (1 mM) | 0.85 ± 0.15 |
| Compound of Ex. 1 | (1 mM) | 1.17 ± 0.13 |
| Compound of Ex. 6 | (0.28 mM) | 1.43 ± 0.12 |

We claim:

1. A compound of the formula (1):

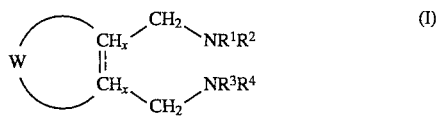

wherein $R^1$, $R^2$, $R^3$ and $R^4$, which may be the same or different represent hydrogen atoms or alkyl groups of 1–6 carbon atoms, x is 0 or 1 and when x is 0 the dashed line represents a double bond and either (a) W represents a group of formula $-(CH_2)_n-$ wherein n is 2 or 3 wherein n is 2 or 3 and x is 0 (thus completing a cyclobut-1-ene or cyclopent-1-ene ring), provided that when n is 2, $R^1$, $R^2$, $R^3$ and $R^4$ all represent alkyl groups of 1 to 6 carbon atoms; or (b) W represents a group of formula or W represents a group of formula $-CH_2-CH_yCH_yR^5\text{---}CH_yR^6-CH_2-$ wherein y is 0 or 1 and when y is 0 the dashed line completes a double bond, the sum of x and y is 0 or 1 (whereby W thus completes a cyclohexene or cyclohexadiene ring) and $R^5$ and $R^6$, which may be the same or different, represent hydrogen atoms or alkyl groups of 1 to 4 carbon atoms, provided that when simultaneously (i) $R^1$, $R^2$, $R^3$ and $R^4$ represent said alkyl groups, (ii) x is 1 and (iii) y is 0, then $R^5$ and $R^6$ represent alkyl groups of 1 to 4 carbon atoms, in the form of the free base or as an acid addition salt tolerable to plants.

2. The compound according to claim 1, which is 1,2-bis(aminomethyl)-4,5-dimethylcyclohexa-1,4-diene, in the form of the free base or an acid addition salt tolerable to plants.

3. The compound according to claim 1, which is trans-1,2-dimethyl-4,5-bis(aminomethyl)cyclohex-1-ene, in the form of the free base or an acid addition salt tolerable to plants.

* * * * *